(12) United States Patent
Poggio et al.

(10) Patent No.: US 6,223,735 B1
(45) Date of Patent: May 1, 2001

(54) CONTROL METHOD FOR AN OXYGEN LINEAR SENSOR

(75) Inventors: Luca Poggio, Spinetta Marengo; Marco Secco, Nizza Monferrato; Daniele Ceccarini, Rimini, all of (IT)

(73) Assignee: Magneti Marelli S.p.A., Milan (IT)

( * ) Notice: Subject to any disclaimer, the term of this patent is extended or adjusted under 35 U.S.C. 154(b) by 0 days.

(21) Appl. No.: 09/354,440

(22) Filed: Jul. 16, 1999

(30) Foreign Application Priority Data

Jul. 1, 1969 (IT) .............................................. BO98A0435

(51) Int. Cl.$^7$ ..................................................... F02D 41/00
(52) U.S. Cl. ............................................. 123/694; 123/696
(58) Field of Search ..................................... 123/694, 696; 73/23.32

(56) References Cited

U.S. PATENT DOCUMENTS

| | | | |
|---|---|---|---|
| 4,723,521 | * | 2/1988 | Mieno et al. .......................... 123/694 |
| 4,796,587 | * | 1/1989 | Nakajima et al. ..................... 123/694 |
| 4,922,429 | * | 5/1990 | Nakajima et al. ..................... 123/694 |
| 4,939,658 | * | 7/1990 | Sekozawa et al. .................... 123/694 |
| 5,199,409 | * | 4/1993 | Miyashita et al. .................... 123/694 |
| 5,524,472 | | 6/1996 | Hötzel . | 
| 5,558,752 | | 9/1996 | Wang et al. . |
| 5,580,440 | * | 12/1996 | Ueno et al. .......................... 123/694 |

* cited by examiner

Primary Examiner—John Kwon
(74) Attorney, Agent, or Firm—Venable; George H. Spencer; Robert Kinberg (57) ABSTRACT

Control method for an oxygen linear sensor, in which the sensor is located along an exhaust duct of an internal combustion engine to receive into a separate chamber part of the exhaust gas and generate a first signal representative of the swing between the composition of the gases in the chamber and a reference stoichiometric composition; the first signal being processed by a retroactive circuit which pilots an electrical current Ip into the sensor in such a manner as to generate an oxygen ion draining mechanism from and towards the chamber and to cancel the swing; the current being converted into an output signal which saving an error due to current spreads, is proportional to the quantity of oxygen present in the exhaust gases; the method presenting the calculation phase of a correction parameter which is applied to the output signal to make it effectively proportional to the quantity of oxygen present in the exhaust gases; the calculation of the parameter being effected with the sensor located in a controlled atmosphere by means of processing of the output signal and of a nominal voltage defining the theoretical value of the output signal in the presence of the said controlled atmosphere.

15 Claims, 3 Drawing Sheets

CONTROL METHOD FOR AN OXYGEN LINEAR SENSOR

The present invention relates to a method of control of an oxygen linear sensor.

In particular the present invention relates to a control method for an oxygen linear sensor known as "UEGO" sensor (universal exhaust gas oxygen ensor), to which explicit reference is made hereinafter though without loss of its general nature.

BACKGROUND OF THE INVENTION

The present invention is of advantage in the automotive field, where it is known to use a UEGO sensor, located along the exhaust duct of an internal combustion engine, to obtain information concerning the composition of the exhaust gases.

The UEGO sensor has two electrolytic cells responding to oxygen ions, and a diffusion chamber interposed between the actual cells and able to receive part of the combustion gases at the outlet from the engine. In addition, the UEGO sensor provides for the use of a test arrangement which is connected to the sensor itself by means of a connector, and is able to pilot, that is control, electrically one of two electrolytic cells to ensure a control action on the sensor. In particular the control means is designed to originate an oxygen ion drainage mechanism from the diffusion chamber to atmosphere and vice versa, in order to obtain within the chamber an exhaust gas composition equal to that which would be obtained in the event of the air/petrol ratio of the mixture fed to the engine becoming stoichiometric, i.e. equal to 14.57.

The intensity of the test action, that is to say the intensity of the control current required to maintain the stoichiometric level within the diffusion chamber, is the information on the basis whereof the test arrangement generates a Vout signal representative of the composition of the exhaust gases proceeding from the engine.

At present the aforesaid control arrangement, before installation on the vehicle, needs to be connected to a compensation resistance able to compensate eventual spreads of variations control current to ensure that the Vout signal is truly representative of the composition of engine exhaust gases. In effect, in the absence of a compensation resistance, the Vout signal would not be effectively representative of the percentage of oxygen in the exhaust gases owing to the swing in control current from the theoretical value due to inevitable losses in the control arrangement. The said compensation resistance, of which the nominal value is indicated by the sensor manufacturer for production purposes, is inserted between two connections of the said connector, and cooperating with the control arrangement, intervenes actively in the generation of the Vout signal recovering the losses in control current.

However, the compensation resistance, in addition to representing an additional cost and involving the installation operations, is subjected to strong thermal stress during the operation of the engine in that it is located in the engine compartment. Consequently, on varying the temperature of the engine it occurs that the compensation resistance assumes differing values in relation to the nominal value which ensures a correct compensation. This involves the control current spreads not being compensated adequately and the Vout signal not being effectively indicative of the true oxygen percentage in the exhaust gases and, consequently, of the effective rating of the mixture.

SUMMARY OF THE INVENTION

The purpose of the present invention is to provide a control method for an oxygen linear sensor which will allow the aforementioned disadvantage to be removed, or that will allow the generation of a Vout signal which is effectively indicative of the quantity of oxygen of present in the exhaust gases, without the use of the compensation resistance.

According to the present invention there is provided a method for controlling an oxygen linear sensor arrangement including an oxygen linear sensor located along an exhaust duct of an internal combustion engine, the sensor having at least a first electrolytic cell, a second electrolytic cell and a diffusion chamber receiving an exhaust gas flowing in the exhaust duct, the sensor supplying a first signal correlated to a difference between a composition of the exhaust gas within the diffusion chamber and a reference stoichiometric composition, the method including the steps of: sensing the first signal; supplying a controlled current, as a function of the first signal, to the sensor to activate oxygen ions draining between the diffusion chamber, the first electrolytic cell and the second electrolytic cell, in a manner to vary the composition of the gas within the diffusion chamber for cancelling the difference between the composition of the exhaust gas within the diffusion chamber and the reference stoichiometric composition; using the controlled current to generate a first output signal correlated to an oxygen content of the exhaust gas; supplying a controlled gas to the sensor, the controlled gas having a controlled composition; recording a behavior of the first output signal during an interval of time in which the sensor is surrounded by the controlled gas; averaging the first output signal during the timed interval to obtain a mean value; calculating a correction parameter on the basis on the mean value and of a nominal value representing a theoretical value of a first output signal in the presence of the controlled gas; and correcting the first output signal by using the correction parameter to produce a corrected output signal proportional to the exhaust gas oxygen content.

BRIEF DESCRIPTION OF THE DRAWINGS

The present invention is now described with reference to the appended drawings, and illustrate a non-restrictive example of operation wherein.

DETAILED DESCRIPTION OF THE INVENTION

Figure 1:
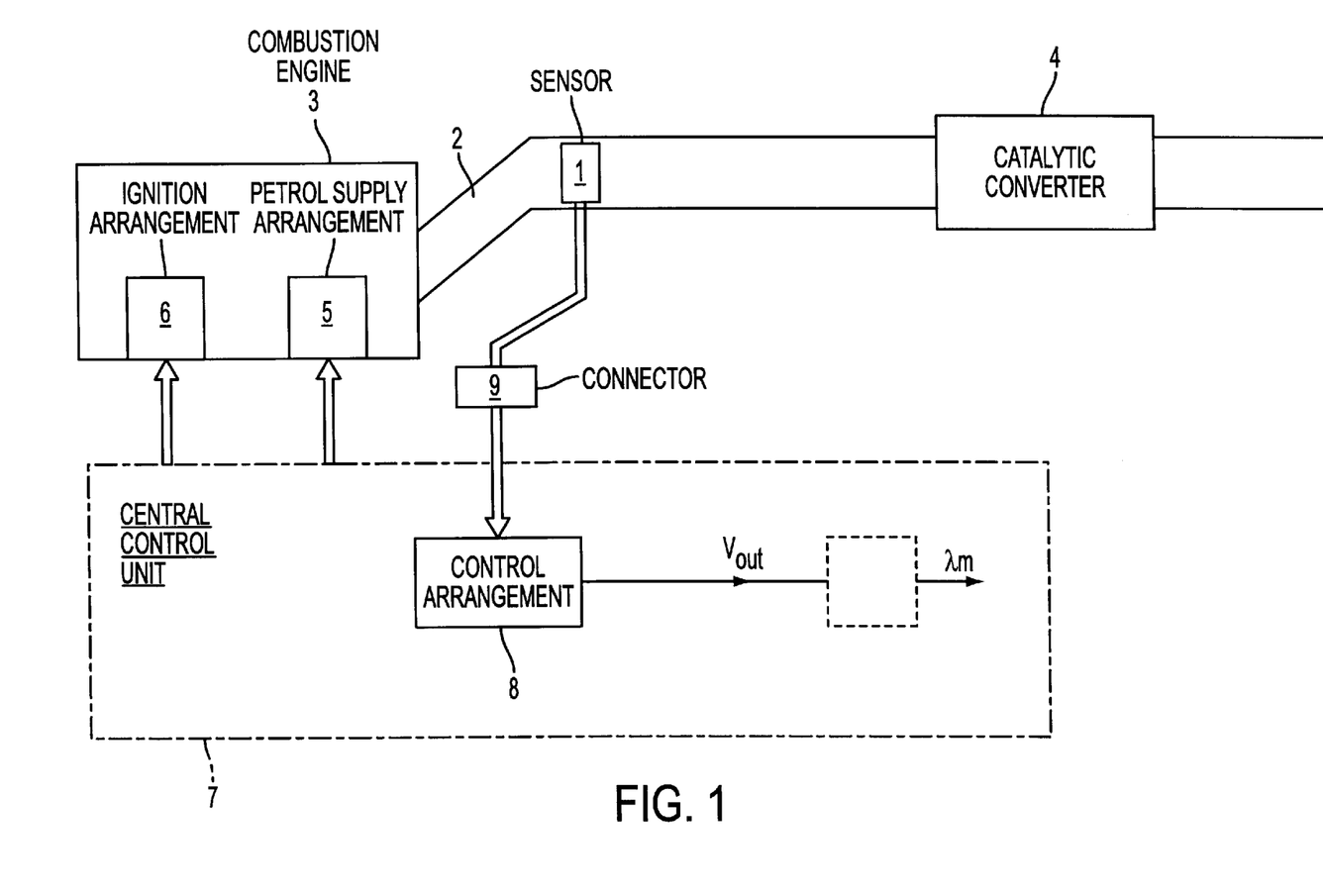
FIG. 1 illustrates diagrammatically the application of a UEGO sensor along the exhaust duct of an internal combustion engine.

With reference to FIG. 1, an UEGO sensor of known type bears the general reference 1 and is able to be placed along an exhaust duct 2 of an internal combustion engine 3 (for example a petrol engine) to obtain information concerning the stoichiometric composition of the composition gases, and finally concerning the A/F (air/fuel) ratio of the mixture fed to the engine.

In the example illustrated here the sensor 1 is located upstream of a catalytic converter 4 able to reduce polluting substances present in the combustion gases before they are emitted into atmosphere. It remains clear that the sensor 1 could also be located downstream of the catalytic converter 4 to measure the percentage of oxygen present in the exhaust gases emitted into atmosphere after the catalytic process. The engine 3 has a petrol supply arrangement 5 to the cylinders (not illustrated), and an ignition arrangement 6 to ignite combustion within the cylinders.

The engine 3 is controlled by electronic control unit 7 (diagrammatically illustrated), which controls the supply arrangement 5 to regulate in the injection time and consequently, the quantity of fuel to be injected into the cylinders, and controls the ignition arrangement 6 to regulate the ignition moments for combustion within the cylinders.

The electronic control unit 7 comprises an electric control arrangement 8 connected to sensor 1 by means of a connector 9 and able to implement the control method of this invention. The control arrangement 8, as better specified hereinafter, is able to process information originating from the sensor 1 to generate an output Vout signal which, according to the present invention, is a digital signal correlated with the quantity of oxygen present in the combustion gases and indicative of the A/F ratio. In particular, the Vout signal is the digital conversion of a corresponding analog signal proportional to the quantity of oxygen present in the combustion gas.

Figure 2:
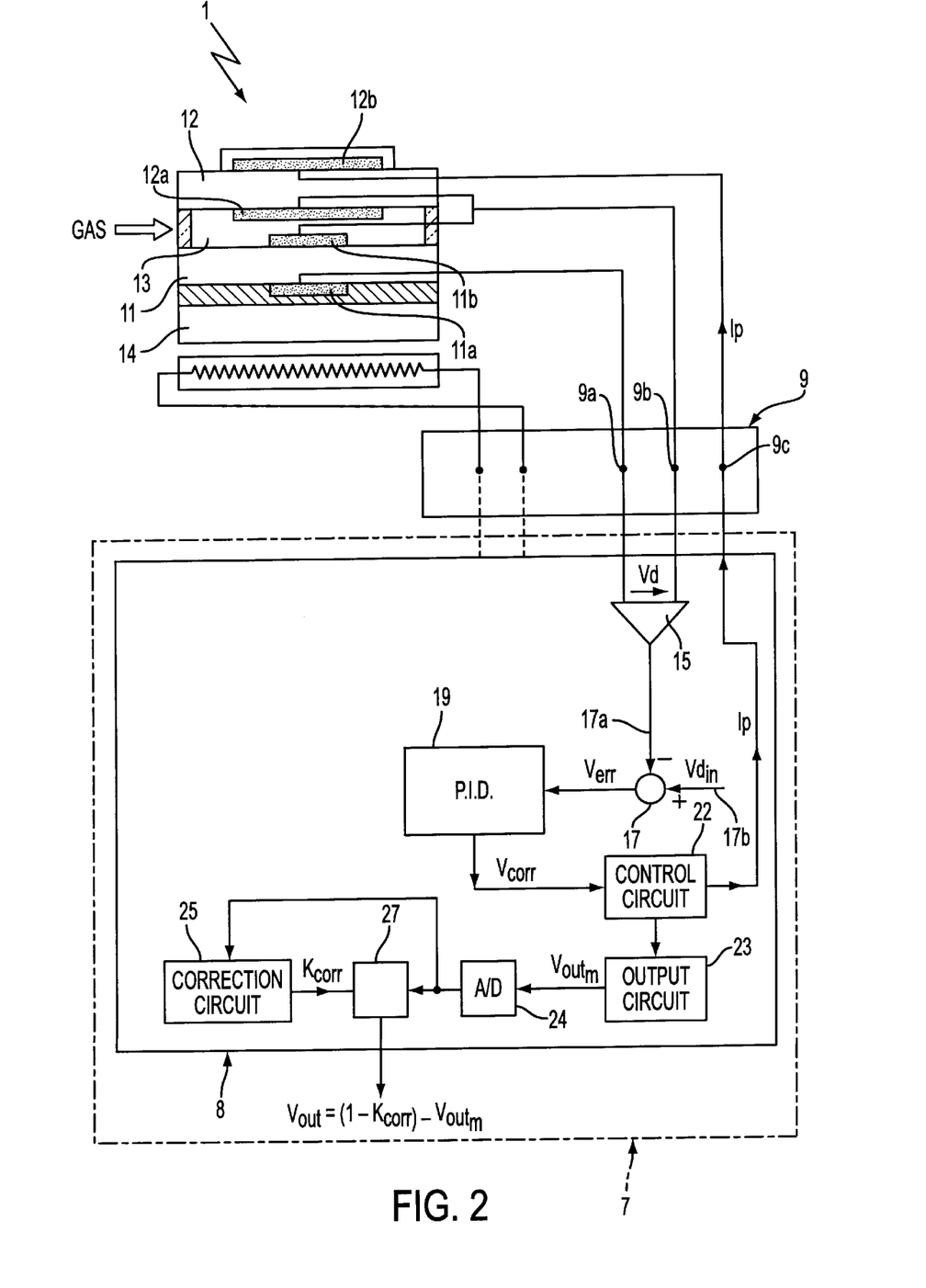
FIG. 2 illustrates diagrammatically a control arrangement for an UEGO sensor achieving the method which is the purpose of the present invention.

The Vout signal is thus determined by the central control unit 7, and in particular is converted (in a known manner) into a λm parameter representative of the air/fuel (A/F) ratio of the global mixture supplied to the engine 3 and defined as:

$$\lambda m = \frac{(A/F)mis}{(A/F)stech}$$

where (A/F)mis represents the value of measured air/petrol ratio obtained by the sensor 1 and correlated with the Vout signal and with (A/F)stech representing the value of the air/fuel stoichiometric ratio equal to 14.57. In particular, if the value of the λm exceeds unity (λm >1) the measured A/F ratio is greater than the A/F stoichiometric ratio and the mixture supplied to the engine 3 is said to be lean, whereas if the value of parameter λm is lower than unity (λm <1) the measured A/F ratio is lower than the A/F stoichiometric ratio and the mixture supplied to the engine 3 is said to be rich. FIG. 2 illustrates in greater detail the connection of the UEGO sensor 1 to the control arrangement 8 by means of the connector 9.

With reference to FIG. 2, the sensor 1 has two electrolytic cells 11 and 12 responding to oxygen ions, respectively termed "Vs sensing cell" and "pumping cell Ip", and a diffusion chamber 13 interposed between the cells 11 and 12 and able to receive the exhaust gas. The sensor 1 also has a reference chamber 14, which is located on the opposite side of the diffusion chamber 13 in relation to cell 12, and is in a stoichiometric condition, i.e. presenting an oxygen level equal to that which the exhaust gas would have in the event of the A/F ratio of the mixture fed to the engine being stoichiometric.

The cell 11 presents at its heads a pair of electrodes 11a and 11b electrically connected to respective connections 9a, 9b of the connector 9. In turn the cell 12 has at its heads a pair of electrodes 12a and 12b, of which the electrode 12a is connected electrically to the electrode 11b of cell 11, whereas electrode 12b is connected to a connection 9c of the connector 9.

In service, between the connections 9a and 9b, that is to say at the heads of the sensing cell 11, there is a signal Vd (voltage) of which the value depends on the swing of the composition of exhaust gas in the diffusion chamber 13 away from the stoichiometric level of the reference chamber 14.

The control arrangement 8, detailed below, has the dual function of electrical supply to the sensor 1 and ensuring a feedback control action designed to modify the composition of the gases within the diffusion chamber 13. In particular the arrangement 8 is able to control a pumping current Ip to the electrode 12b of cell 12 to achieve an oxygen ions draining mechanism within the diffusion chamber 13 out to atmosphere (and vice versa) in such a way as to achieve a stoichiometric level within chamber 13.

The intensity of the control action, that is to say the intensity of the pumping current Ip required to maintain a stoichiometric level within the diffusion chamber 13 is the information on the basis whereof the control arrangement 8 generates the output Vout signal.

The control arrangement 8 comprises an amplifier 15 which is connected as input to connections 9a and 9b of the connector 9 to receive the Vd signal (voltage), and is able to supply the amplified Vd signal to the subtracter input 17a of a summation node 17. In particular, the amplified signal Vd assumes values of around 450 mV whenever within the diffusion chamber 13 there are gases originating from the combustion of a stoichiometric mixture, and in the meantime assumes values greater than 450 mV (or respectively lower than 450 mV) when the gases originate from the combustion of a rich mixture (or respectively a lean mixture).

The summation node 17 has a summation input 17b to which is supplied a reference signal $Vd_{rif}$, which represents the reference (or set point) for the amplified Vd signal, and is equal to the amplified value of the signal Vd which is present at the heads of the cell 12 in the event that the exhaust gases emitted from the diffusion chamber 13 originate from the combustion of a stoichiometric mixture. In the example shown here, according to the aforementioned description, la the reference signal $Vd_{rif}$ assumes the value 450 mV.

The node 17 generates an output error signal Verr, which is defined by the difference between the reference signal Vdrif and the amplified Vd signal, and is represented of the error between the voltage in the heads of cell 11 in the event of stoichiometric conditions and that which effectively is recorded at the heads of cell 12.

The error signal Verr is supplied to a processing circuit 19 able to process it to provide an output correction signal Vcorr. In the illustrated example the processing circuit 19 is defined by a PID controller of known type able to effect a proportional integral derivative transformation (PID) of the Verr signal to generate the Vcorr signal.

The Vcorr correction signal is supplied to a control circuit 22 (of known type), which, on the basis of the Vcorr signal, regulates the intensity of the pumping current Ip supplied to cell 12. In particular, the Vcorr signal is the input on the basis whereof the control circuit 22 corrects the current Ip so that the cell 12 drains the oxygen ions from the diffusion chamber 13 to atmosphere (or vice versa) to achieve the stoichiometric conditions in chamber 13. In the example illustrated here the control circuit is represented by a voltage/current converter of known type able to convert the Vcorr voltage signal into a corresponding current Ip to be supplied to cell 12.

In this way a feedback control is achieved which tends to cancel the error signal Verr. According to this feedback control, whenever exhaust gases injected into the diffusion chamber 13 are derived from the combustion of a lean mixture, the Verr error signal is above zero, and the PID controls the control circuit 22 in order the current Ip fed to cell 12 generates a flow of oxygen ions from chamber 13 to atmosphere. In that way by means of the feedback control, the chamber 13 tends to be returned to a stoichiometric condition. Vice versa, whenever the discharge gases are lower in oxygen, or are derived from combustion of a rich mixture, the error signal Verr is lower than zero, and the PID controls the control circuit 22 so that the current Ip fed to cell 12 generates a flow of oxygen ions from atmosphere towards the diffusion chamber 13. In that way by means of the feedback control, there is a tendency to return chamber 13 to the stoichiometric condition. The control circuit 22, also, cooperates with an output circuit 23, which in a known manner, converts the pumping current Ip into a $Vout_m$ signal correlated with the composition of the combustion gases present in the exhaust duct 2, or the quantity of oxygen present in the gases output from the engine 3. The output circuit 23 is thus able to translate the force induced by the control arrangement 8 to maintain a stoichiometric condition in the diffusion chamber 13, into a $Vout_m$ signal, which is converted in an analog/digital converter 24 into a $Vout_m$ digital signal, which, saving the correction explained below, represents the output signal Vout from the arrangement 8.

In this invention the control arrangement 8 has a correction circuit 25 (detailed below) able to ensure correction of the digital-converted $Vout_m$ signal so as to ensure that when the engine 3 is running, the Vout signal output from the arrangement 8 itself assumes values effectively representative of the quantity of oxygen present in the exhaust gases. In the absence of the correction circuit 25, owing to the spreads of the current Ip (or of the swing from a true value to a theoretical value of current Ip), the $Vout_m$ signal would not effectively express the true percentage of oxygen present in the exhaust gases and therefore would tend to produce an incorrect measurement of the $\lambda$m parameter. The correction circuit 25 receives its input the $Vout_m$ signal output from the converter 25, and its function is to calculate a correction Kcorr parameter able to be applied to the $Vout_m$ signal itself to obtain the Vout signal allowing compensation of the Ip current spreads. In particular, in the example illustrated here, the Kcorr parameter is applied to the $Vout_m$ digital-converted signal within a processing block 27 which will provide the Vout signal output according to the following expression:

$$Vout=Vout_m \cdot (1-Kcorr) \quad (1)$$

According to the invention, to calculate the correction parameter Kcorr, the sensor 1 needs to be in a controlled atmosphere of which the oxygen percentage is initially known, in such a way that within the diffusion chamber 13, the entry of gases of known stoichiometric composition is possible. In fact when the percentage of oxygen in gases entering the chamber 13 is known, it is also basically known what nominal value Vnom the required signal $Vout_m$ should take in the presence of such a controlled atmosphere. The correction circuit 25, as explained further on, calculates the correction parameter Kcorr on the basis of the swing of the signal $Vout_m$ in relation to the nominal value Vnom. When the motor is running, as the sensor 1 is surrounded by gases of which the oxygen percentage is to be defined, the digital-converted $Vout_m$ signal is always correct thanks to the Kcorr parameter (according to expression (1)) to originate the Vout signal and make good the spreads of the piloting current Ip. According to the invention to arrange for the sensor 1 to be surrounded by gas of which the oxygen percentage is initially known, there are two possible alternative methodologies.

In the first methodology, before its installation in the exhaust duct 2 of the engine 3, the sensor 1 is kept for a given period T in a controlled atmosphere (for example in air) so that the diffusion chamber 13 is surrounded by gases of known oxygen content. During interval T, the correction circuit 25 measures signal $Vout_m$, and knowing the nominal value Vnom expected of the $Vout_m$ signal for a given oxygen content, the Kcorr correction parameter value is defined. Having once calculated the Kcorr parameter the sensor is installed along the exhaust duct 2.

With the second methodology, however, the Kcorr parameter calculation is made with the sensor 1 already installed in a exhaust duct 2, making use of the fact that for a given engine running condition (known as "cut-off") the sensor 1 is surrounded by a flow of pure air. In effect, when the engine is in the "cut-off" condition or when the accelerator pedal is raised, the central control 7 calls for the supply arrangement 5 to impose a zero injection time. Consequently, the inside of the cylinders does not receive petrol and the air aspirated by the engine passes directly into the exhaust manifold 2 without undergoing any combustion.

Figure 4:
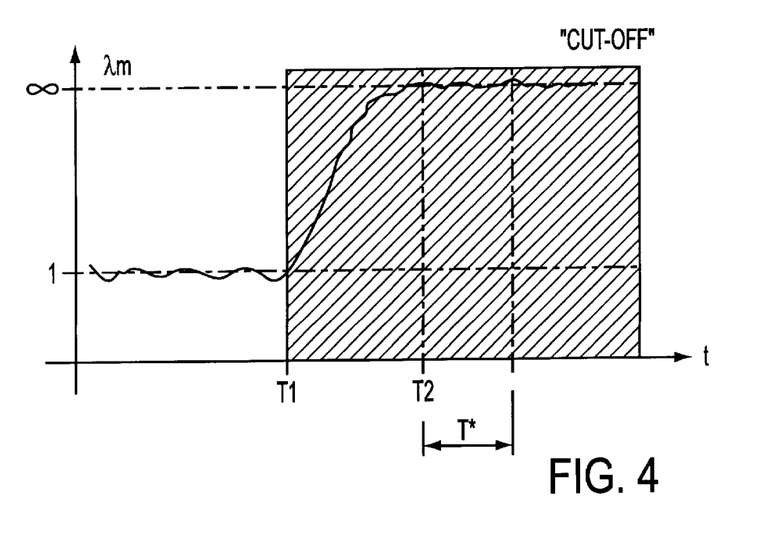
FIG. 4 represents the performance in time of the rating of the mixture fed to the engine when the engine itself is in a particular operating mode.

This situation is shown in FIG. 4, which illustrates the $\lambda$m range discharge procedure as a function of time. If at moment T1 the injection time is set at zero defining the entry into "cut-off", the air intake flow starts washing the discharge duct 2 of residual petrol vapours. In that way the $\lambda$m ratio to discharge, which before the T1 moment was approximately unity, starts rising, and with a dynamic function of the number of revolutions of the engine and the pressure within the intake duct, an extremely high value is reached (tending towards infinity $\infty$.

In the manner of instant T2, or 3 or 4 seconds after instant T1, the $\lambda$m ratio to discharge reaches such extremely high values (as represented by the infinity symbol $\infty$ in FIG. 4). After the T2 instant the sensor 1 is surrounded by a flow of pure air of which the oxygen content is known. The correction circuit 25 measures the $Vout_m$ signal for a given interval T* and knowing the nominal value Vnom that the signal $Vout_m$ should achieve for such oxygen percentages, determines the value of the correction parameter Kcorr. Once the Kcorr parameter is known, it will be possible to effect the compensation of the Ip current spread according to the expression (1) regardless of the running condition of the engine 3, and therefore, whatever the composition of the discharge gases may be.

As a rule the Kcorr parameter is calculated when the engine 3 is in the "cut-off" condition for the first time after ignition of the engine 3.

Figure 3:
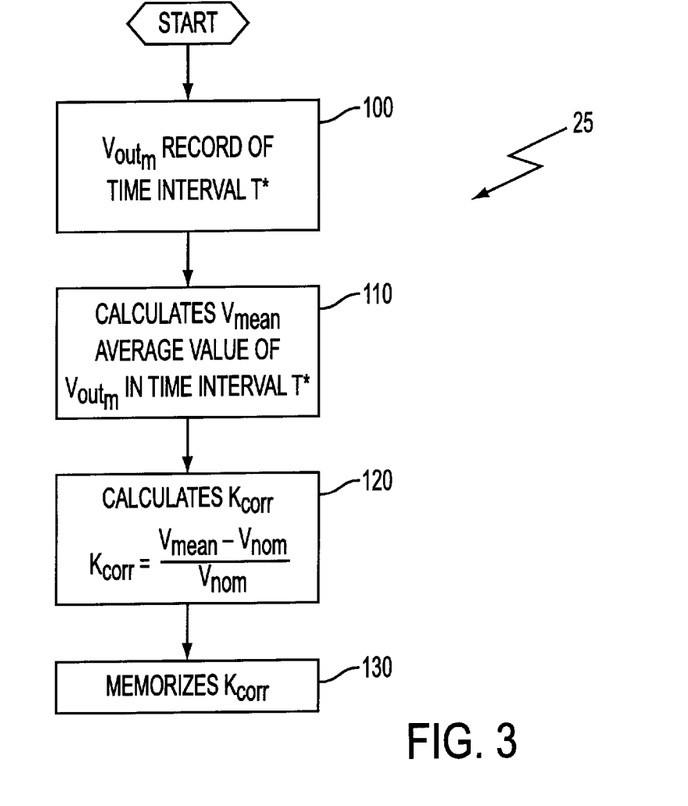
FIG. 3 is a block diagram of the operations occurring in a circuit forming part of the arrangement in FIG. 2.

With reference to FIG. 3, the operation of the correction circuit 25 is now described.

From an initial START block a move is made to block 100 when the sensor 1 is surrounded by gas of which the oxygen percentage is known. In the first methodology, the transfer to block 100 occurs after a given time from the moment at which the sensor 1 is brought into a controlled atmosphere, whereas with the second methodology the said transfer occurs at the specific moment T2 (FIG. 4).

In block 100 the course of the digital converted signal $Vout_m$ for the time interval T* is determined (see FIG. 4), and may assume differing amplitudes, generally a few seconds for both methodologies.

The move is made from block 100 to block 110, wherein the mean value Vmean of the signal $Vout_m$ in time interval T*, is calculated in a known manner.

From block 110 the move continues to block 120, wherein the correction parameter Kcorr is calculated based on the mean value Vmean and the nominal value Vnom (basically known) required of the $Vout_m$ signal, on knowing the oxygen percentage of gases coming to sensor 1. In block 120 the Kcorr parameter is calculated according to the following expression:

$$Kcorr = \frac{Vmean - Vnom}{Vnom} \quad (2)$$

From block 120 finally the move is made to a block 130 in which the Kcorr parameter obtained according to the expression (2) is stored in a permanent storage block (not illustrated). Compensation of the Ip current spreads is thus always effected with the stored value of the Kcorr parameter using expression (1), and the Vout output signal from the control arrangement 8 is always representative of the λm ratio of the mixture provided to the engine, or effectively proportional to the quantity of oxygen present in the exhaust gases. It is clear that the present invention allows avoidance of the need for control arrangement 8 to cooperate with the cited compensation resistance, as occurs in control arrangements of known type, thus allowing a saving from the economic viewpoint.

What is claimed is:

1. Method for controlling an oxygen linear sensor arrangement including an oxygen linear sensor, located along an exhaust duct of an internal combustion engine, the sensor having at least a first electrolytic cell, a second electrolytic cell and a diffusion chamber receiving an exhaust gas flowing in the exhaust duct, the sensor supplying a first signal correlated to a difference between a composition of the exhaust gas within the diffusion chamber and a reference stoichiometric composition, the method comprising the steps of:

sensing the first signal;

supplying a controlled current, as a function of the first signal, to the sensor to activate oxygen ions draining between the diffusion chamber, the first electrolytic cell and the second electrolytic cell, in a manner to vary the composition of the gas within the diffusion chamber for canceling the difference between the composition of the exhaust gas within the diffusion chamber and the reference stoichiometric composition;

using the controlled current to generate a first output signal ($Vout_m$) correlated to an oxygen content of the exhaust gas;

supplying a controlled gas to the sensor, the controlled gas having a controlled composition;

recording a behavior of the first output signal ($Vout_m$) during an interval of time in which the sensor is surrounded by the controlled gas;

averaging the first output signal ($Vout_m$) during the time interval to obtain a mean value;

calculating a correction parameter on the basis of the mean value and of a nominal value representing a theoretical value of the first output signal ($Vout_m$) in the presence of the controlled gas; and correcting the first output signal ($Vout_m$) by using the correction parameter to produce a corrected output signal proportional to the exhaust gas oxygen content.

2. Method according to claim 1, wherein the controlled gas is defined by gas of which the oxygen percentage is known; and the method includes placing the sensor in the controlled gas before installation of the sensor within the exhaust duct of the engine.

3. Method according to claim 2, wherein the controlled gas is defined by air in which the sensor is maintained before installation of the exhaust duct of the engine (3); and the calculating step includes calculating the correction parameter when the sensor is maintained in contact with air for said interval of time.

4. Method according to claim 1, wherein the controlled gas is defined by pure air which is emitted by the engine along the exhaust duct when the engine is in a specifically defined operating condition (cut-off).

5. Method according to claim 4, wherein the correction parameter is calculated when the sensor is surrounded by the air emitted by the engine along the exhaust duct following an interruption in a supply of fuel to the cylinders of the engine.

6. Method according to claim 5, wherein said interval of time in which the first output signal ($Vout_m$) is recorded following interruption of the fuel supply to the cylinders of the engine is distanced in time from a moment when the interruption of the fuel supply occurs.

7. Method according to claim 4, wherein the correction parameter is calculated when the engine is for the very first time in the operating condition termed "cut-off" with an interruption of the fuel supply to the cylinders following completion of ignition of the engine.

8. Method according to claim 1, further including storing the calculated correction parameter and applying the stored correction parameter to the first output signal ($Vout_m$) to compensate for current spreads of the controlled current during the running of the engine.

9. Method according to claim 1, wherein the correction parameter is calculated according to the following expression:

$$Kcorr = \frac{Vmean - Vnom}{Vnom}$$

wherein Vnom is said nominal value and Vmean is said mean value.

10. Method according to claim 1, wherein when the sensor is surrounded by exhaust gases from the engine of which it is required to have details as to the stoichiometric composition, the correction parameter is applied to the the first output signal ($Vout_m$) according to the expression:

$$Vout = Vout_m(1 - Kcorr)$$

where Vout represents the corrected $Vout_m$ output signal.

11. Method according to claim 1, wherein the controlled current is supplied to the first cell to vary the composition of the gases within the diffusion chamber by way of an oxygen ions draining mechanism which drains oxygen ions from and/or towards the diffusion chamber, and the second electrolytic cell supplies the first signal; and the method further includes regulating the controlled current supplied to the first electrolytic cell with a feedback circuit receiving the first signal as an input so as to cancel a swing of the controlled current by way of the oxygen draining mechanism.

12. Method according to claim 1, wherein the controlled current is supplied to the first electrolytic cell to vary the composition of the gas within the diffusion chamber, and the second electrolytic cell supplies the first signal which is representative of the difference between the composition of the gas within the diffusion chamber and the reference stoichiometric composition, and the method further includes regulating the controlled current supplied to the first electrolytic cell with a feedback circuit receiving the first signal as an input.

13. Method according to claim 12, wherein the regulating step includes
(i) amplifying the first signal;
(j) generating a reference signal corresponding to a value of the first amplified signal in the case of the presence of a reference stoichimetric composition in the diffusion chamber;
(k) comparing the reference signal with the first amplified signal to generate an error signal;
(l) processing the error signal by a controller; and
(m) regulating the intensity of the controlled current in the first electrolytic cell as a function of the result of processing by the controller, so that the oxygen ions draining from and/or to the diffusion chamber comprises the cancellation of the error signal, creating the reference stoichiometric composition in the chamber.

14. Method according to claim 13, wherein the controller effects a proportional-integral-derivative processing operation of the error signal.

15. Method for controlling an oxygen linear sensor arrangement including an oxygen linear sensor located along an exhaust duct of an internal combustion engine, the sensor having at least a first electrolytic cell, a second electrolytic cell and a diffusion chamber receiving an exhaust gas flowing in the exhaust duct, the method comprising the steps of:

sensing a first signal supplied by the second electrolytic cell of the sensor correlated to a difference between a composition of the exhaust gas within the diffusion chamber and a reference stoichiometric composition;

supplying a controlled current to the first electrolytic cell of the sensor for varying the composition of the exhaust gas within the diffusion chamber by activating oxygen ions draining between the diffusion chamber, the first electrolytic cell and the second electrolytic cell;

regulating the controlled current, with the use of a feedback circuit receiving the first signal as an input, in a manner to vary the composition of the gas within the diffusion chamber for canceling the difference between the composition of the exhaust gas within the diffusion chamber and the reference stoichiometric composition;

using the controlled current to generate a first output signal correlated to an oxygen content of the exhaust gas;

supplying a controlled gas to the sensor, the controlled gas having a controlled composition;

recording a behavior of the first output signal during an interval of time in which the sensor is surrounded by the controlled gas;

calculating a correction parameter on the basis of the recorded behavior of the controlled gas and of a nominal value representing a theoretical value of the first output signal in the presence of the controlled gas; and correcting the first output signal by using the correction parameter to produce a corrected output signal proportional to the exhaust gas oxygen content.

* * * * *

UNITED STATES PATENT AND TRADEMARK OFFICE
CERTIFICATE OF CORRECTION

PATENT NO.    : 6,223,735 B1
DATED         : May 1, 2001
INVENTOR(S)   : Lucca Poggio et al.

It is certified that error appears in the above-identified patent and that said Letters Patent is hereby corrected as shown below:

<u>Title page,</u>
Item [30] Foreign Application Priority Data, should read as follows: July 16, 1998

Signed and Sealed this

Twenty-ninth Day of January, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO. : 6,223,735 B1
APPLICATION NO. : 09/354440
DATED : May 1, 2001
INVENTOR(S) : Luca Poggio, Marco Secco and Daniele Ceccarini It is certified that error appears in the above-identified patent and that said Letters Patent is hereby corrected as shown below:

Please add the following to item (56) References Cited:

FOREIGN PATENT DOCUMENTS

JP Patent Abstract Publ. No. 58161859    9/1983
JP Patent Abstract Publ. No. 58162858    9/1983

Signed and Sealed this

Fifth Day of June, 2007

JON W. DUDAS
*Director of the United States Patent and Trademark Office*